United States Patent [19]

Beguin et al.

[11] 4,230,596
[45] Oct. 28, 1980

[54] FAMILY OF LIQUID CRYSTALS OF THE DISUBSTITUTE DIESTER TYPE

[75] Inventors: Alain Beguin; Jean-Claude Dubois; Annie Zann, all of Paris, France

[73] Assignee: Thomson-CSF, Paris, France

[21] Appl. No.: 933,564

[22] Filed: Aug. 14, 1978

[30] Foreign Application Priority Data

Aug. 17, 1977 [FR] France .................................. 77 25180

[51] Int. Cl.³ .................... C07C 69/90; C07C 121/60; C09K 3/34
[52] U.S. Cl. .............................. 252/299; 260/465 D; 350/350 R; 560/65
[58] Field of Search .................... 252/299; 260/465 D; 560/65

[56] References Cited

U.S. PATENT DOCUMENTS

| | | | |
|---|---|---|---|
| 3,915,883 | 10/1975 | Van Meter et al. | 252/299 |
| 3,953,491 | 4/1976 | Steinsträsser et al. | 260/465 D |
| 3,971,824 | 7/1976 | Van Meter et al. | 560/65 |
| 4,017,416 | 4/1977 | Inukai et al. | 252/299 |
| 4,073,742 | 2/1978 | Erdmann et al. | 252/299 |
| 4,110,243 | 8/1978 | Abert-Mellah et al. | 252/299 |

OTHER PUBLICATIONS

Dubois et al., Mol. Cryst. Liq. Cryst., vol. 42, p. 139 (1977).

Primary Examiner—Dolph H. Torrence
Attorney, Agent, or Firm—Oblon, Fisher, Spivak, McClelland & Maier

[57] ABSTRACT

A family of organic compounds having at least one mesomorphic phase of nematic type and, in respect of some compounds, one or more smetic phases. The liquid crystals according to the invention satisfy general formula:

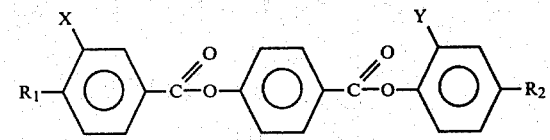

in which $R_1$ is an alkyl or alkoxy group having n carbon atoms (n being an integer of 1 to 10) X designates the bromine or the cyano group, Y is a methyl group.

10 Claims, No Drawings

FAMILY OF LIQUID CRYSTALS OF THE DISUBSTITUTE DIESTER TYPE

The invention relates to a family of liquid crystals of the "disubstituted diester" type constituted by organic compounds having three benzene nuclei bonded by —COO— groups. The pure compounds, the mixture of these compounds with each other liquid crystals, and the synthesis of the organic compounds of the family are part of the invention, as are the electro-optical devices employing such liquid crystals.

Most of the organic compounds of the family have at least one mesomorphic phase of the nematic type. Further, some compounds have in addition to the nematic phase one or more mesomorphic phases of the smectic type. In their mesomorphic phase, some compounds have a large negative dielectric anisotropy.

According to the invention, there is provided a family of liquid crystals of the "disubstituted diester" type, comprising organic compounds satisfying the general chemical formula:

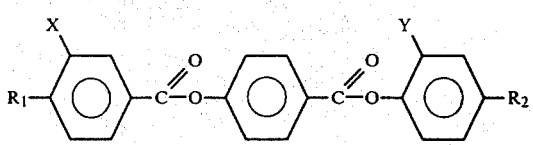

in which
- $R_1$ designates an alkyl group or alkoxy group having n carbon atoms, n being an integer of 1 to 10;
- $R_2$ designates an alkyl group having m carbon atoms, m being an integer of 1 to 10;
- X designates bromine or the cyano group;
- Y designates the methyl group.

The substances of the family thus defined are designated by:
4-n-alkyl-2-methyl benzene-4-(3 bromo-4-n alkoxy benzoyloxy) in the case where $R_1$ is the alkoxy group $C_nH_{2n+1}O$ and X the bromine atom;
4-n-alkyl-2-methylbenzene-4-(3-bromo-4-n alkylbenzoyloxy) in the case where $R_1$ is the alkyl group $C_nH_{2n+1}$, and X the bromine atom;
4-n-alkyl-2-methylbenzene-4-(3-cyano-4-n alkoxy benzoyloxy) in the case where $R_1$ is the alkoxy group $C_nH_{2n+1}O$, and X the cyano group
4-n-alkyl-2-methylbenzene-4-(3-cyano-4-n alkylbenzoyloxy) in the case where $R_1$ is the alkyl group $C_nH_{2n+1}$ and X the cyano group.

The general outline of the process for manufacturing the compounds according to the invention is described hereinafter and then a few examples of the mode of operating relative to specific cases of synthesis will be given.

GENERAL PROCESS OF MANUFACTURE

There is made the synthesis of 4-n-alkyl-2-methylbenzene-4-hydroxybenzoate then, according to the case, of 3-bromo-4-n-alkoxy-benzoic or 3-bromo-4-n-alkyl benzoic acid, under the conditions described hereinafter to obtain the 4-n-alkyl-2-methylbenzene-3-bromo-4-n-(alkyl or alkoxy) benzoate.

To obtain the compounds having CN instead of Br, the bromine is replaced in the brominated compounds as described schematically hereinafter.

Synthesis of 4-n-alkyl-2-methylbenzene-4-hydroxybenzoate

The following reactions are produced in succession in which R designates an alkyl group and $R_2$ the R-$CH_2$ group:

(1) Friedel-Craft reaction:

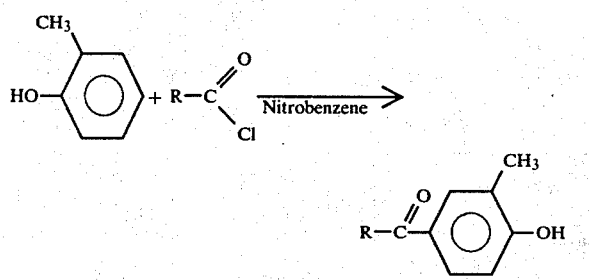

In this way 4-hydroxy-3-methyl-alkanophenone is obtained.

(2) Wolff-Kishner reaction:

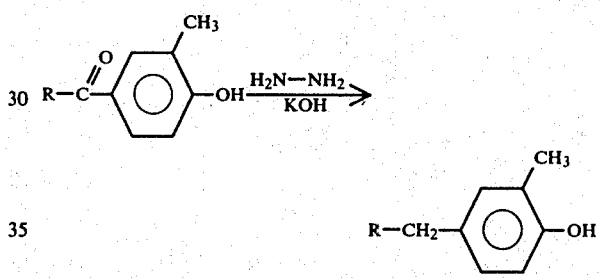

There is thus obtained a product the formula of which is rewritten as follow

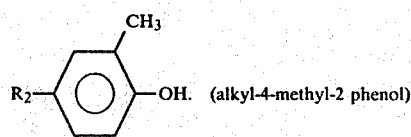

(alkyl-4-methyl-2 phenol)

where $R_2$ designates an alkyl (3) Esterification reaction:
Using the product of the second reaction:

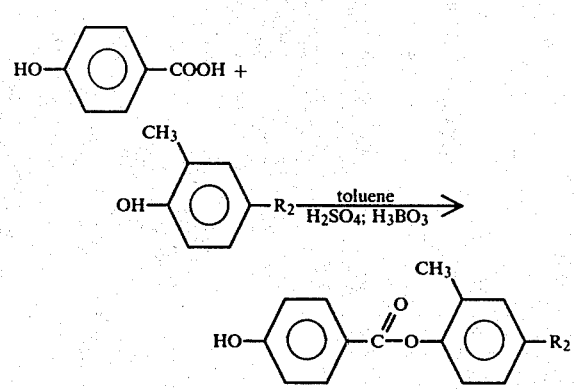

Synthesis of 3-bromo-4-n alkyl-benzoic acid

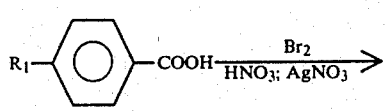

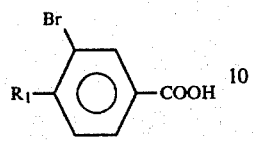

in which $R_1 = C_nH_{2n+1}$

Synthesis of 3-bromo-4-n-alkoxy-benzoic acid

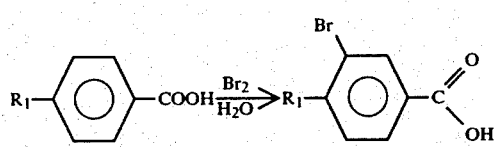

Synthesis of 3-bromo-4-n-alkyl-benzoyl chloride

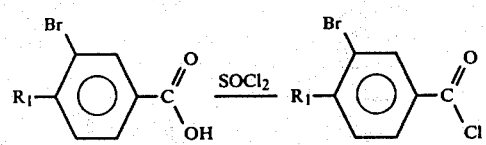

Synthesis of 3-bromo-4-n-alkoxy-benzoyl chloride

By the same reaction as above, there is obtained:

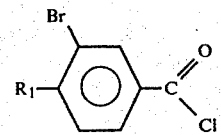

Final synthesis (1) Case of X=Br and Y=CH₃:

An esterification reaction is carried out between 4-n-alkyl-2-methylbenzene-4-hydroxy benzoate obtained at the step (30°) here above and one of the chlorides synthetized hereinbefore:

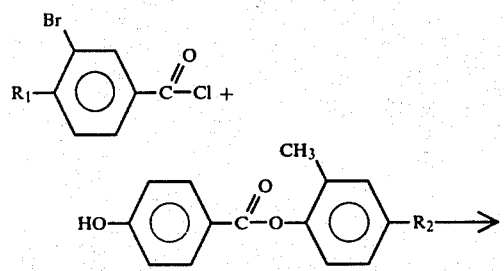

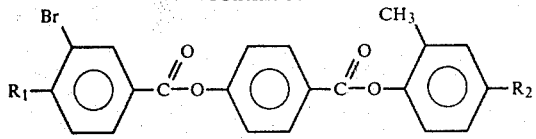

with
$R_1 = C_nH_{2n+1}O$ or $C_nH_{2n+1}$
$R_2 = C_mH_{2m+1}$

There is thus obtained 4-n-alkyl-2-methylbenzene-(3-bromo-4n-alkoxy or alkyl benzoyloxy)

(2) Case of X=CN and Y=CH₃:

The brominated compound obtained above is debrominated.

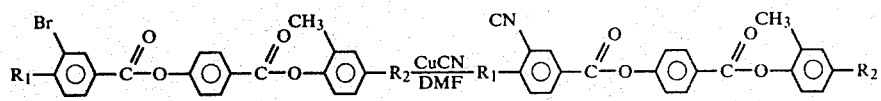

with
$R_1 = C_nH_{2n+1}O$ or $C_nH_{2n+1}$
$R_2 = C_mH_{2m+1}$ and DMF=dimethylformamide In this way there is obtained the 4-n-alkyl-2-methyl benzene-4-(3-cyano-4-n-alkylbenzoyloxy)

EXAMPLES OF MODES OF OPERATING (1) Synthesis of 4-hydroxy-3-methyl-pentanophenone (based on the Friedel-Craft reaction)

108 g (1 mole) of orthocresol are added to a liter of nitrobenzene. The solution is cooled to 0° C. and 280 g (2.1 moles) of powdered aluminium chloride are added over a period of one hour (while stirring). While still stirring and at 0° C., 120.5 g (1 mole) of valeryl chloride are added over a period of one hour 30 minutes. The temperature of the solution is left for about 12 hours at this temperature. The solution is then poured into a mixture of 1 kg of ice and 500 ml of 37% hydrochloric acid. The mixture is stirred for one hour and the organic phase is decanted. It is whashed with 5 N hydrochloric acid and then with deionized water.

The nitrobenzene is thereafter distilled. 176.5 g of crude product is obtained which is recrystallized in 500 cc of a 50—50 hexane/benzene mixture. In this way 162.5 g of pure compound is obtained. The yield of the synthesis is on the order of 85%.

(2) Synthesis of 4-n-pentyl-2-methyl-phenol 153.6 g (0.8 moles) of 4-hydroxy-3-methyl-pentanophenone are added to 500 ml of diethylene glycol, 120 g (3.8 moles) of hydrazine and 196 g (3.5 moles) of potash. The solution is refluxed at 135° C. in the mass for 2 hours and then the excess hydrozine and water are distilled until the temperature of the mass is 230° C. The solution is allowed to cool and then poured into 2.5 l of deionized water. It is then acidified with concentrated hydrochloric acid to pH1. The product precipitates. It is extracted with ether. The ethereal extract is washed with deionized water and then dried on magnesium sulphate. The ether is distilled and the product is purified by distillation. It distills at 97.5° C. at 0.4 mm of mercury. 121.6 g of pure compound is obtained, namely a yield of 85%.

(3) Esterification reaction 9.8 g ($5.5 \cdot 10^{-2}$ moles) of 4-pentyl-2-methyl-phenol, 6.9 g ($5 \cdot 10^{-3}$ moles) of p-hydroxy benzoic acid, 0.25 g of concentrated sulphuric acid and 0.15 g of boric acid are added to 350 ml of toluene. The solution is refluxed for 120 hours while decanting the water formed in the course of the reaction. The toluene is then distilled. 16.7 g of crude product is obtained which is purified by chromatography on a column of silica. 10 g of pure product, namely a yield of 67% is obtained.

Synthesis of 4-octyloxy-3-bromo-benzoic acid 37.5 g (0.15 mole) of p-octyloxy benzoic acid are put in suspension in 108 ml of deionized water. The temperature of the reaction medium is brought to between 50° C. and 55° C. and 8.7 ml (0.17 mole) of bromine are added at this temperature over a period of 7 hours 30 minutes.

The product is then filtered, washed with deionized and recrystallized in ethanol. 37.9 g of pure product are obtained.

Synthesis of 4-octyl-3-bromo-benzoic acid 7 g (0.03 mole) of p-octyl benzoic acid and 6.4 g (0.04 mole) of bromine are added to a mixture of 15 ml of deionized water, 20 ml of nitric acid and 90 ml of acetic acid, the temperature of which is 25° C. A solution of 5.1 g (0.03 mole) of silver nitrate in 15 ml of deionized water is then added over a period of half an hour. The solution is stirred for 3 hours 30 minutes, then the solid in suspension is filtered and washed with deionized water until the washing water shows a neutral reaction. The acid is dissolved in ethanol and the solution is bleached while hot with vegetable black. The crude product obtained after distillation of the ethanol is recrystallized in a 75% ethanol/25% water mixture. 5.1 g of pure product are obtained.

Synthesis of 4-n-pentyl-2-methylbenzoate-4-(3-bromo-4-n-heptyloxy benzoyloxy)

2.98 g (0.01 mole) of 4-hydroxy-benzoate of 2-methyl-4-n-pentyl benzene are dissolved in 20 ml of pyridine. 3.35 g (0.01 mole) of 4-heptyloxy-3-bromo-benzoyl chloride are then added. The solution is stirred for 70 hours at room temperature and then poured into a mixture of 70 g of ice and 8 cc of concentrated sulphuric acid. After stirring for one hour, the product is extracted with benzene. The benzenic extracts are then washed with deionized water and then dried on magnesium sulfate. After distillation of the benzene, 6.1 g of crude product are obtained and the product is purified by chromatography on a column of silica and recrystallization. 5.1 g of pure compound, namely a yield of 86% are obtained.

Synthesis of 4-n-pentyl-2-methylbenzoate-4(3-cyano-4-n-heptyloxy benzoyloxy)

2.975 g ($5 \cdot 10^{-3}$ moles) of the pure product obtained in the former synthesis and 0.6 g ($6.7 \cdot 10^{-3}$ moles) of cuprous cyanide are added to 10 ml of dimethyl formamide. The solution is refluxed for 6 hours. It is allowed to cool and then poured into a mixture of 60 cc of deionized water and 5.5 cc of ethylene diamine. The solution is stirred for one hour and then extracted with ether. The extract is washed, dried and then the ether is distilled. 2.6 g of crude product are obtained and the product is purified by chromatography on a column of silica and recrystallization. 1.6 g of pure product, namely a yield of 61% are obtained.

The temperature ranges in degree Celsius of a certain number of compounds according to the invention are shown in the following table:

| Reference | Compounds | Transition temperatures (see note) |
|---|---|---|
| A | $C_7H_{15}O$—⟨Ph(Br)⟩—C(=O)—O—⟨Ph⟩—C(=O)—O—⟨Ph(CH_3)⟩—$C_5H_{11}$ | K 89,5 N 113 I |
| B | $C_8H_{17}O$—⟨Ph(Br)⟩—C(=O)—O—⟨Ph⟩—C(=O)—O—⟨Ph(CH_3)⟩—$C_5H_{11}$ | K 95 N 112,5 I |
| C | $C_8H_{17}$—⟨Ph(Br)⟩—C(=O)—O—⟨Ph⟩—C(=O)—O—⟨Ph(CH_3)⟩—$C_5H_{11}$ | K 61,5 N 68 I |
| D | $C_7H_{15}O$—⟨Ph(CN)⟩—C(=O)—O—⟨Ph⟩—C(=O)—O—⟨Ph(CH_3)⟩—$C_5H_{11}$ | K 101,5 $S_A$ 116 N 116,5 |
| E | $C_8H_{17}O$—⟨Ph(CN)⟩—C(=O)—O—⟨Ph⟩—C(=O)—O—⟨Ph(CH_3)⟩—$C_5H_{11}$ | K 72,5 $S_A$ 122 I<br>$S_C$ 41 $S_A$ |
| F | $C_8H_{17}$—⟨Ph(CN)⟩—C(=O)—O—⟨Ph⟩—C(=O)—O—⟨Ph(CH_3)⟩—$C_5H_{11}$ | K 84,5 I<br>$S_A$ 61 N 64 I |

Note:
K = solid crystalline phase
$S_C$ = smectic phase C
$S_A$ = smectic phase A
N = nematic phase
I = isotropic phase The dielectric constants of the compound of reference "E" mixed with a liquid crystal "J" having a nematic phase between 29° and 43° C., were measured: it concerns p-pentylphenol p-methoxybenzoate. The composition of the mixture is 90% of compound "J" for 10% of the compound according to the invention.

The following table gives the result of measurements carried out at 24° C. for the liquid crystal "J" in superfusion and for a mixture such as defined hereinbefore.

The measurements were carried out in an orienting magnetic field of 10,000 oersteds, a periodic electric field (F=10 KHz) being applied to the liquid crystal.

| Liquid crystal | $\epsilon$ parallel | $\epsilon$ perpendicular | $\Delta\epsilon$ |
| --- | --- | --- | --- |
| "J" | 5.7 | 5.6 | +0.1 |
| Mixture "E + J" | 5.6 | 6.6 | −1.0 |

It is concluded from the last two results of the fourth column that the negative dielectric anisotropy of the pure product "E" must be very high since the influence of this product on the anisotropy of the mixture is also high, where as it is only in a very small proportion in the liquid crystal thus obtained. The result would be similar if the compound according to the invention were in a proportion of 5 to 15% in the mixture.

When the frequency of the electric field is varied, a still more negative anisotropy is observed, and in particular between 60 and 100 KHz, for the liquid crystal "E+J", it is −2.2.

The compounds according to the invention, when pure or in mixture with other liquid crystals, may be used for manufacturing electrooptical devices, in particular for displays and readouts.

What we claim is:

1. A liquid crystal compound of the formula

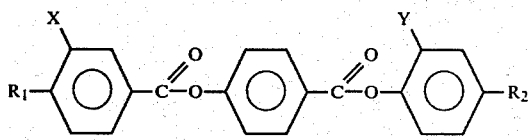

in which
   $R_1$ designates an alkyl group or alkoxy group having n carbon atoms, n being an integer of 1 to 10;
   $R_2$ designates an alkyl group having m carbon atoms, m being an integer of 1 to 10;
   X designates bromine or the cyano group;
   Y designates the methyl group.

2. A liquid crystal compound of claim 1, wherein
   $R_1$ is $C_7 H_{15} O$;
   $R_2$ is $C_5 H_{11}$;
   X is Br and
   Y is $C H_3$.

3. A liquid crystal compound of claim 1, wherein
   $R_1$ is $C_8 H_{17} O$;
   $R_2$ is $C_5 H_{11}$;
   X is Br and
   Y is $C H_3$.

4. A liquid crystal compound of claim 1, wherein
   $R_1$ is $C_8 H_{17}$;
   $R_2$ is $C_5 H_{11}$;
   X is Br and
   Y is $C H_3$.

5. A liquid crystal compound of claim 1, wherein
   $R_1$ is $C_7 H_{15} O$;
   $R_2$ is $C_5 H_{11}$;
   X is C N and
   Y is $C H_3$.

6. A liquid crystal compound of claim 1, in which
   $R_1$ is $C_8 H_{17} O$;
   $R_2$ is $C_5 H_{11}$;
   X is C N and
   Y is $C H_3$.

7. A liquid crystal compound of claim 1, wherein
   $R_1$ is $C_8 H_{17}$;
   $R_2$ is $C_5 H_{11}$;
   X is C N and
   Y is $C H_3$.

8. A mixture comprising a liquid crystal compound of claim 1, with p-pentylphenol-p-methoxybenzoate.

9. A mixture as claimed in claim 8, comprising 5 to 15% of said liquid crystal compound.

10. An electro-optical device comprising a liquid crystal compound of claim 1.

UNITED STATES PATENT AND TRADEMARK OFFICE
CERTIFICATE OF CORRECTION

PATENT NO. : 4,230,596

DATED : October 28, 1980

INVENTOR(S) : Alain Beguin et al

It is certified that error appears in the above-identified patent and that said Letters Patent is hereby corrected as shown below:

Column 1, lines 41, 44, and 47 and 50, after "benzoyloxy)"(each occurrence), insert -- benzoate --

Column 4, lines 12 and 29, after "benzoyloxy)" (each occurrence), insert -- benzoate --.

Column 6, lines 4 and 22, after "benzoyloxy)" (each occurrence), insert -- benzoate --.

Signed and Sealed this

Ninth Day of November 1982

[SEAL]

Attest:

GERALD J. MOSSINGHOFF

Attesting Officer     Commissioner of Patents and Trademarks